United States Patent
Tanaka (10) Patent No.: US 11,452,437 B2
(45) Date of Patent: Sep. 27, 2022

(54) LIGHT SOURCE APPARATUS FOR ENDOSCOPE, ENDOSCOPE, AND ENDOSCOPE SYSTEM

(71) Applicant: OLYMPUS CORPORATION, Tokyo (JP)

(72) Inventor: Yoshinori Tanaka, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 77 days.

(21) Appl. No.: 17/144,268

(22) Filed: Jan. 8, 2021

(65) Prior Publication Data
US 2021/0127960 A1 May 6, 2021

Related U.S. Application Data

(63) Continuation of application No. PCT/JP2018/025911, filed on Jul. 9, 2018.

(51) Int. Cl.
| | | |
|---|---|---|
| *A61B 1/07* | (2006.01) | |
| *A61B 1/06* | (2006.01) | |
| *G02B 23/24* | (2006.01) | |
| *G02B 23/26* | (2006.01) | |

(52) U.S. Cl.
CPC .............. *A61B 1/07* (2013.01); *A61B 1/0655* (2022.02); *A61B 1/0669* (2013.01); *A61B 1/0684* (2013.01); *G02B 23/2469* (2013.01); *G02B 23/26* (2013.01)

(58) Field of Classification Search
CPC .... A61B 1/07; A61B 1/0655; G02B 23/2469; G02B 23/26
See application file for complete search history.

(56) References Cited

U.S. PATENT DOCUMENTS

| | | | |
|---|---|---|---|
| 9,921,098 B2 * | 3/2018 | Tanaka | A61B 1/0653 |
| 2011/0220779 A1 | 9/2011 | Takaoka | |
| 2013/0345517 A1 | 12/2013 | Morimoto et al. | |
| 2014/0054450 A1 * | 2/2014 | Shirota | G02B 23/26 |
| | | | 250/226 |

(Continued)

FOREIGN PATENT DOCUMENTS

| | | |
|---|---|---|
| EP | 0844472 A1 | 5/1998 |
| JP | H07-294329 A | 11/1995 |

(Continued)

OTHER PUBLICATIONS

International Search Report dated Sep. 25, 2018 issued in PCT/JP2018/025911.

*Primary Examiner* — William N Harris
(74) *Attorney, Agent, or Firm* — Scully, Scott, Murphy & Presser, P.C.

(57) ABSTRACT

A light source apparatus for an endoscope includes an optical fiber that guides emission light emitted from a light source and is incident on a fiber end face, a ferrule having a ferrule end face having a through-hole in which the optical fiber is inserted, a holder to which the ferrule is fixed, the holder having a reflecting surface that reflects first reflected light to thereby emit second reflected light, the first reflected light being the emission light reflected on the fiber end face, and an optical sensor that receives the second reflected light disposed between the light source and the fiber end face and in a region facing the reflecting surface through an optical axis.

15 Claims, 9 Drawing Sheets

(56) References Cited

U.S. PATENT DOCUMENTS

| | | | |
|---|---|---|---|
| 2016/0037999 A1* | 2/2016 | Yabe | A61B 1/00006 600/109 |
| 2018/0136454 A1* | 5/2018 | Yoshida | A61B 1/06 |
| 2021/0085160 A1* | 3/2021 | Kamee | A61B 1/0684 |

FOREIGN PATENT DOCUMENTS

| | | |
|---|---|---|
| JP | H08-327826 A | 12/1996 |
| JP | 2001-324654 A | 11/2001 |
| JP | 2005-10484 A | 1/2005 |
| JP | 2007-163358 A | 6/2007 |
| JP | 2011-192848 A | 9/2011 |
| JP | 2012-143414 A | 8/2012 |
| JP | 2014-301 A | 1/2014 |

* cited by examiner

LIGHT SOURCE APPARATUS FOR ENDOSCOPE, ENDOSCOPE, AND ENDOSCOPE SYSTEM

CROSS REFERENCE TO RELATED APPLICATION

This application is a continuation application of PCT/JP2018/025911 filed on Jul. 9, 2018, the entire contents of which are incorporated herein by this reference.

BACKGROUND OF THE INVENTION

1. Field of the Invention

The present invention relates to a light source apparatus for an endoscope including an optical sensor, an endoscope including the light source apparatus for the endoscope including the optical sensor, and an endoscope system including the light source apparatus for the endoscope including the optical sensor.

2. Description of the Related Art

In the light source apparatus for the endoscope, it is necessary to appropriately manage the amount of illumination light. In an endoscope system including a light source apparatus having a xenon lamp as a light source, the illumination light generated by the light source apparatus is guided to a distal end portion via a plurality of optical fiber bundles that is inserted through a universal cord and an insertion portion. The amount of light is controlled by, for example, adjusting the optical aperture of the light source apparatus based on the brightness of the endoscope image. That is, the amount of light of the xenon lamp is substantially stable, and does not change greatly depending on the usage conditions.

On the other hand, a light source apparatus for an endoscope using a light emitting device such as a semiconductor laser diode (LD) as a light source has been studied. The LD and the like generate heat during driving, and the amount of light changes depending on their own temperature. To deal with this, the amount of light is detected in real time, and a drive signal to be supplied to the light source is controlled based on the detection result. In order to detect the amount of light from the light source, a light receiving device such as a photodiode is used.

A large amount of light is used for the illumination light for the endoscope as compared with the signal light used for data communication. Thus, when the arrangement position of the light receiving device changes, the absolute value of the amount of light received by the light receiving device changes largely. However, the light amount range (dynamic range) in which the light receiving device can accurately detect the amount of light is not wide. Therefore, it is not easy to accurately detect the amount of illumination light outputted from the light emitting device by using the light receiving device.

Japanese Unexamined Patent Application Publication No. 7-294329 discloses an optical power monitor apparatus that detects the amount of signal light guided by an optical fiber by a photodiode disposed on a side surface of a glass ferrule in which the optical fiber is inserted. The signal light incident from the ferrule end face is reflected on the inner peripheral surface of the ferrule and guided to a position where the photodiode is disposed.

That is, by a lens having the numerical aperture equal to or larger than the numerical aperture of the optical fiber, some of the signal light is focused on the ferrule end face around the incident surface of the optical fiber. In order to reflect the signal light on the inner peripheral surface of the ferrule, the outer peripheral surface of the ferrule is covered with a reflective member.

SUMMARY OF THE INVENTION

A light source apparatus for an endoscope according to an embodiment includes an optical fiber having a fiber end face, the optical fiber guiding emission light emitted from a light source and incident on the fiber end face, a ferrule having a ferrule end face, the ferrule having an opening of a through-hole on the ferrule end face, the optical fiber being inserted into the through-hole, a holder to which the ferrule is fixed, the holder having a reflecting surface configured to reflect first reflected light to thereby emit second reflected light, the first reflected light being the emission light reflected on the fiber end face, and an optical sensor having a light receiving surface that receives the second reflected light, the optical sensor being disposed between the light source and the fiber end face and in a region facing the reflecting surface through an optical axis.

An endoscope according to the embodiment includes a light source apparatus for the endoscope, and the light source apparatus for the endoscope includes an optical fiber having a fiber end face, the optical fiber guiding emission light emitted from a light source and incident on the fiber end face, a ferrule having a ferrule end face, the ferrule having an opening of a through-hole on the ferrule end face, the optical fiber being inserted into the through-hole, a holder to which the ferrule is fixed, the holder having a reflecting surface configured to reflect first reflected light to thereby emit second reflected light, the first reflected light being the emission light reflected on the fiber end face, and an optical sensor having a light receiving surface that receives the second reflected light, the optical sensor being disposed between the light source and the fiber end face and in a region facing the reflecting surface through an optical axis.

An endoscope system according to the embodiment includes an endoscope and a light source apparatus for the endoscope, and the light source apparatus for the endoscope includes an optical fiber having a fiber end face, the optical fiber guiding emission light emitted from a light source and incident on the fiber end face, a ferrule having a ferrule end face, the ferrule having an opening of a through-hole on the ferrule end face, the optical fiber being inserted into the through-hole, a holder to which the ferrule is fixed, the holder having a reflecting surface configured to reflect first reflected light to thereby emit second reflected light, the first reflected light being the emission light reflected on the fiber end face, and an optical sensor having a light receiving surface that receives the second reflected light, the optical sensor being disposed between the light source and the fiber end face and in a region facing the reflecting surface through an optical axis.

DETAILED DESCRIPTION OF THE PREFERRED EMBODIMENT

<Configuration of Endoscope>

Figure 1:
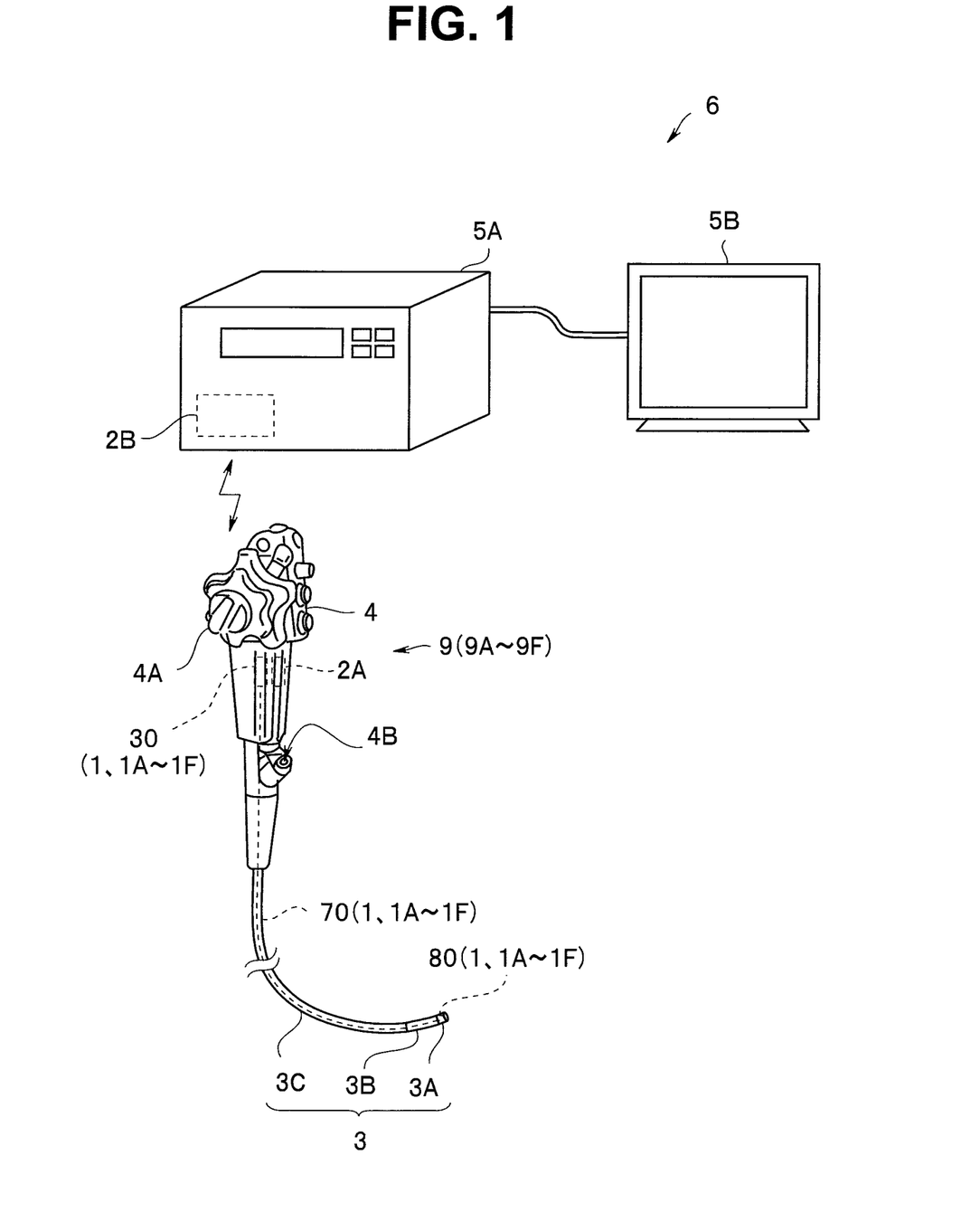
FIG. 1 is a perspective view of an endoscope system including an endoscope according to an embodiment.

As illustrated in FIG. 1, an endoscope system 6 including an endoscope 9 according to an embodiment includes the endoscope 9, a processor 5A, and a monitor 5B. The endoscope 9 has an insertion portion 3 and a grasping portion 4. The endoscope 9 is a so-called cordless endoscope. In the cordless endoscope, an image signal obtained by capturing an in-vivo image of a subject is wirelessly transmitted from a transmitting unit 2A to a receiving unit 2B of the processor 5A. The endoscope 9 incorporates a light source apparatus 1 for the endoscope having a fiber pigtail (hereinafter, referred to as a "light source apparatus 1"), which will be described later in detail.

The cordless endoscope has better operability than the endoscope coupled to the processor and the light source apparatus by a universal cord.

The insertion portion 3 includes a distal end portion 3A, a bending portion 3B that can be bent and is continuously connected with a proximal end portion of the distal end portion 3A, and an elongated flexible portion 3C continuously connected with a proximal end portion of the bending portion 3B. The bending portion 3B can be bent by rotating an angle knob 4A of the grasping portion 4. The grasping portion 4 has a channel opening 4B for a treatment instrument channel through which the insertion portion 3 is inserted.

Although not illustrated in the drawing, an illumination optical system that emits illumination light is disposed at the distal end portion 3A of the endoscope 9.

Figure 2:
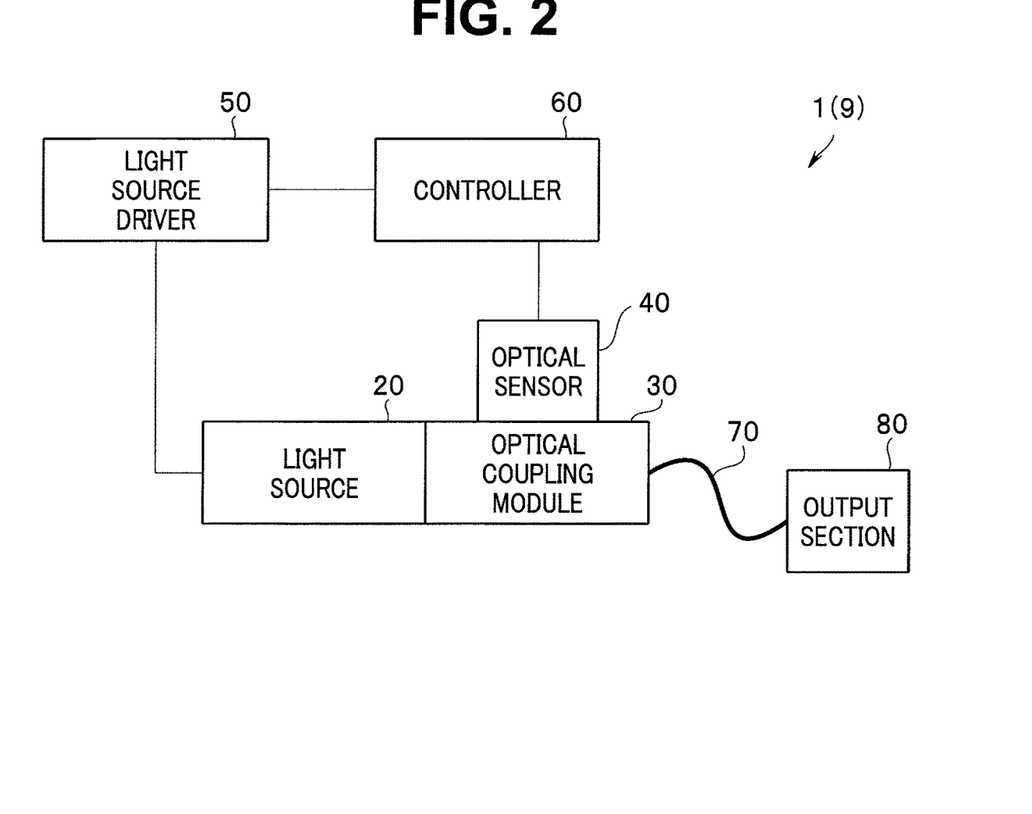
FIG. 2 is a configuration diagram of a light source apparatus for the endoscope according to the embodiment.
Figure 3:
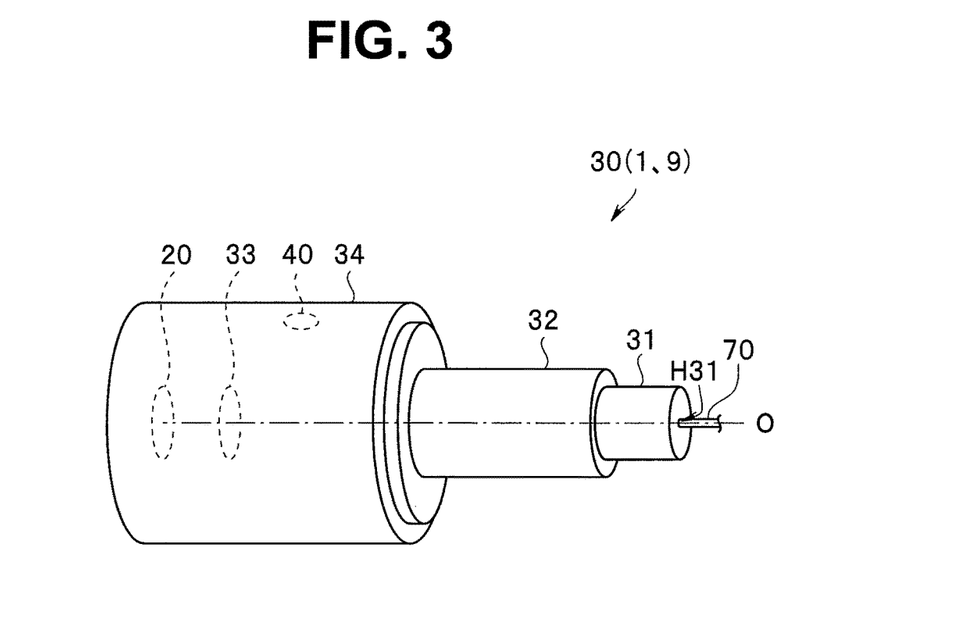
FIG. 3 is a perspective view of the light source apparatus for the endoscope according to the embodiment.

In the light source apparatus 1, main components such as an optical connection module 30 are disposed in the grasping portion 4, and the illumination light is guided to an emission section 80 of the distal end portion 3A via one optical fiber 70 that passes through the insertion portion 3, and is emitted from the illumination optical system (see FIG. 2). The light source apparatus 1 that guides the illumination light using only one optical fiber 70 is minimally invasive because the insertion portion 3 has a small diameter.

Note that, although the endoscope 9 is a flexible endoscope for medical use, an endoscope according to another embodiment may be a rigid endoscope or an endoscope for industrial use. An endoscope according to yet another embodiment may be an endoscope connected to the processor by a universal cord.

<Configuration of Light Source Apparatus for Endoscope>

As illustrated in FIGS. 2 to 5, the light source apparatus 1 according to the embodiment includes the optical connection module 30 as a main component. The optical connection module 30 includes a ferrule 31, a holder 34, an optical sensor 40, and the optical fiber 70.

Note that, in the following description, the drawings based on the respective embodiments are schematic. It should be noted that the relationship between the thickness and width of each portion, the ratio of the thickness of each portion, the relative angle, and the like are different from the actual ones. There may be portions having different dimensions and ratios between the drawings. In addition, illustration of some components and reference numerals may be omitted. For example, a lead wire of the optical sensor 40 is not illustrated.

The optical connection module 30 guides emission light (illumination light) emitted from a light emitting section 20A of the light source 20 to the emission section 80 via the optical fiber 70 which is a light guide member.

The optical fiber 70 may be made of either glass or resin, and may be either multimode or single-mode, as long as the illumination light can be guided to the emission section 80. When the optical fiber 70 is the multimode fiber, it may be either a step-index or a graded-index. It is particularly preferable that the optical fiber 70 be a step-index multimode fiber in order to guide a large amount of illumination light.

For example, the emission section 80 is provided with a phosphor that generates yellow light when receiving blue light emitted from the light source 20. Accordingly, white light including blue light and yellow light is emitted from the emission section 80 as illumination light. The light source apparatus 1 may include the light source 20 that emits white light.

The light source 20 is a small semiconductor light emitting device that is a semiconductor laser diode (LD) or a light emitting diode (LED) and that is housed in a package as a CAN package. The semiconductor light emitting device is ultra-compact and has low power consumption compared with a xenon lamp.

The light source 20 may be a so-called bare chip semiconductor light emitting device. The end portion of the waveguide that emits the illumination light guided by passing through the waveguide from another light source may be used as the light source 20. That is, the light source 20 is not limited to the light emitting device or the like that emits light by itself. The optical connection module 30 may be fixed to a light source module including the light source 20 and a lens 33.

Figure 4:
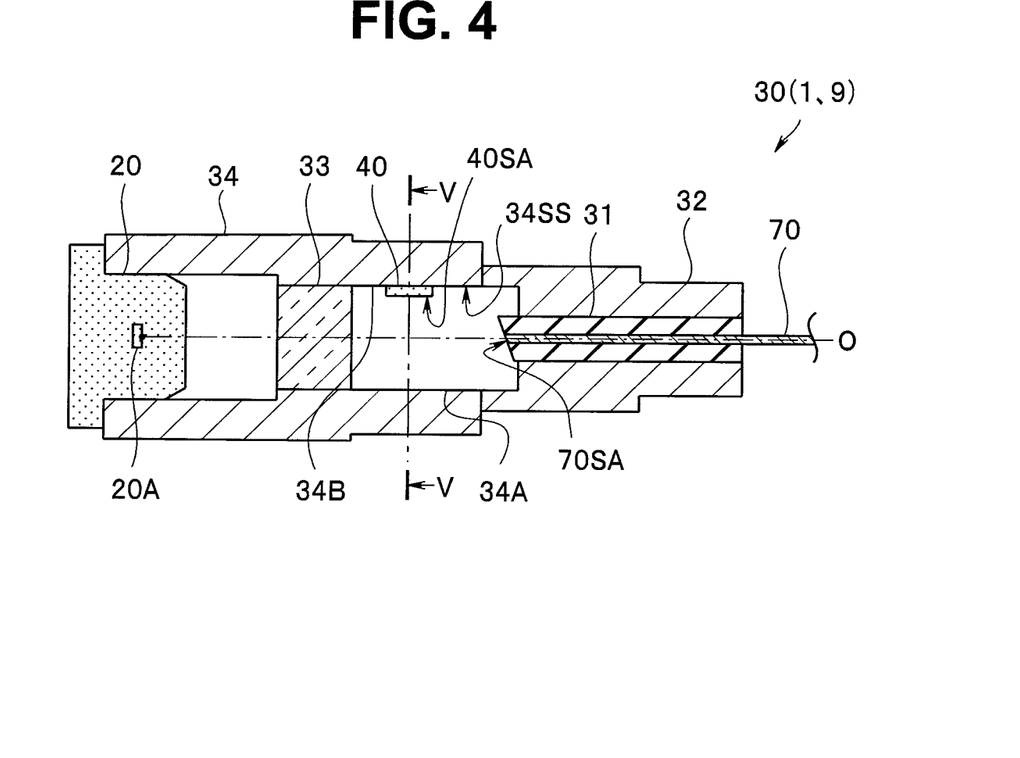
FIG. 4 is a cross-sectional view of the light source apparatus for the endoscope according to the embodiment.

Most of the emission light (illumination light) emitted from the light source 20 is incident on a fiber end face 70SA of the optical fiber 70 by the optical connection module 30, and is guided.

The cylindrical ferrule 31 has a ferrule end face 31SA. The ferrule end face 31SA has an opening of a through-hole H31 into which the optical fiber 70 is inserted. The inner diameter of the through-hole H31 is slightly larger than the outer diameter of the optical fiber 70, and an adhesive (not illustrated) is disposed between the outer peripheral surface of the optical fiber 70 and the inner surface of the through-hole H31.

The holder 34 is a holding member that fixes the light source 20 and the ferrule 31. That is, the ferrule 31 is inserted inside the holder 34. The holder 34 made by processing a metal such as stainless steel or brass has an inner surface 34SS which constitutes a space that is an optical path for the emission light collected by the lens 33.

The optical connection module 30 further includes the lens 33. The lens 33 collects the emission light emitted from the light source 20 on the fiber end face 70SA. The lens 33 may be a single lens, or a lens group including a plurality of lenses as long as the lens has a predetermined numerical aperture.

The numerical aperture (NA) of the lens 33 is equal to or less than the numerical aperture (NA) of the optical fiber 70. That is, the emission light is focused on the fiber end face 70SA (strictly speaking, a core end face of the optical fiber 70 formed of a core and a clad). Thus, the light source apparatus 1 has high efficiency to transfer the illumination light.

The fiber end face 70SA is inclined with respect to a plane perpendicular to an optical axis O of the optical fiber 70. Note that the optical axis O of the optical fiber 70 coincides with a main axis through which the strongest light in the light flux of the emission light focused by the lens 33 passes.

In the light source apparatus 1, first reflected light, which is some of the emission light reflected on the fiber end face 70SA, is further reflected on the inner surface 34SS of the holder 34, so that second reflected light is emitted. That is, a region of the inner surface 34SS on which the first reflected light is incident is a reflecting surface.

The optical sensor 40 including a light receiving device such as a photodiode (PD) receives the second reflected light and outputs a detection signal having an output value corresponding to the amount of light of the second reflected light. The optical sensor 40 may first process the detection signal outputted from the light receiving device, and then output the processed detection signal.

Figure 5:
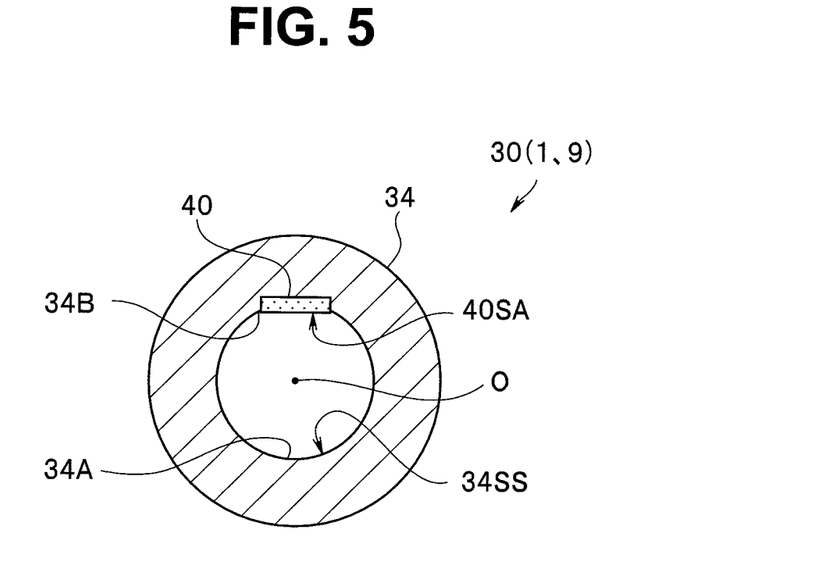
FIG. 5 is a cross-sectional view of the light source apparatus for the endoscope according to the embodiment taken along line V-V of FIG. 4.

In the optical sensor 40, which is chip-based, the light receiving surface 40SA is disposed on the inner surface 34SS between the light source 20 (lens 33) and the fiber end face 70SA in parallel with the optical axis O of the optical fiber 70 (strictly speaking, an extension line of the optical axis O, and the main axis through which the strongest light in the light flux of the emission light focused by the lens 33 passes).

Since the emission light is the illumination light, the amount of light is much larger than that of the signal light, and the light incident on the optical sensor 40 may exceed the upper limit of the dynamic range of the optical sensor 40.

Figure 6:
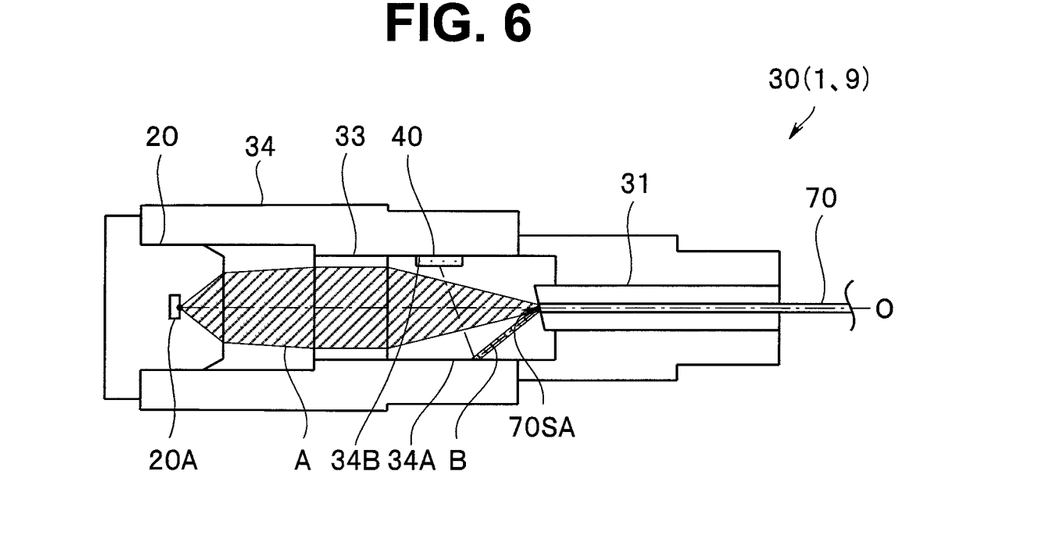
FIG. 6 is a diagram for explaining an optical path of the light source apparatus for the endoscope according to the embodiment.

As illustrated in FIG. 6, in the optical sensor 40 of the light source apparatus 1, the light receiving surface 40SA is disposed so as to face the reflecting surface through the optical axis O. Accordingly, the first reflected light is not directly incident on the optical sensor 40.

Further, the optical sensor 40 is disposed outside an optical path A of the emission light passing from the lens 33 to the optical fiber 70 and outside an optical path B of the first reflected light. The light receiving surface 40SA does not face the inclined fiber end face 70SA. The first reflected light is emitted in the direction of the position facing the arrangement position of the optical sensor 40 through the optical axis O. The first reflected light is reflected on the inner surface 34SS of the holder 34 on which the optical path B impinges, and emits the second reflected light. Then, the second reflected light is incident substantially perpendicular to the light receiving surface 40SA of the optical sensor 40 (for example, the incident angle is more than 60 degrees and less than 120 degrees), so that the second reflected light is efficiently received.

Since the second reflected light is reflected twice, the amount of light is greatly reduced compared with the emission light emitted from the light source 20. Note that the optical sensor 40 may receive multiple reflected light reflected three times or more. Since the multiple reflected light with a large number of reflections has a long optical path, the effect of reducing the amount of light is particularly remarkable.

The light source apparatus 1 further includes a controller 60 that adjusts the amount of emission light by controlling the light source 20 according to the output value of the optical sensor 40. That is, under the control of the controller 60, the drive signal outputted by a light source driver 50 to the light source 20 is adjusted in real time, and the light source 20 generates an appropriate amount of emission light.

Note that the controller 60 and the light source driver 50 may be separated from the optical connection module 30. For example, the controller 60 may be disposed in the processor 5A for the endoscope 9. Further, a CPU of the processor 5A for the endoscope 9 may have the function of the controller 60.

In the light source apparatus 1, the optical sensor 40 receives the second reflected light having an appropriate amount of light, so that the amount of light can be accurately detected. Thus, the light source apparatus 1 can emit illumination light having an appropriate amount of light. The endoscope 9 having the light source apparatus 1 can obtain an endoscope image having appropriate brightness by illumination light having an appropriate amount of light. Note that the appropriate amount of light is the amount of light in the dynamic range of the optical sensor 40, and is preferably the amount of light in the middle of the dynamic range.

Note that the light source apparatus 1 is incorporated in the endoscope 9. However, the light source apparatus according to the embodiment may be separated from the endoscope, and may be detachably attached to the endoscope. That is, the endoscope system may include an endoscope and a light source apparatus separately. The light source apparatus according to the embodiment may be used by being inserted into the treatment instrument channel from the channel opening 4B. For example, the light source apparatus according to the embodiment may be a light source apparatus that irradiates narrow band illumination light, and that is inserted into a treatment instrument channel of an endoscope that performs white light illumination. The light source apparatus according to the embodiment may be a light source apparatus that irradiates, for example, a cauterization laser beam for treatment instead of illumination light.

<Modifications of Embodiment>

Since light source apparatuses 1A to 1F and endoscopes 9A to 9F according to modifications of the embodiment are similar to and have the same effects as the light source apparatus 1 and the endoscope 9 according to the embodiment, the components having the same functions are designated by the same reference numerals and the description thereof will be omitted.

<Modification 1 of Embodiment>

Figure 7:
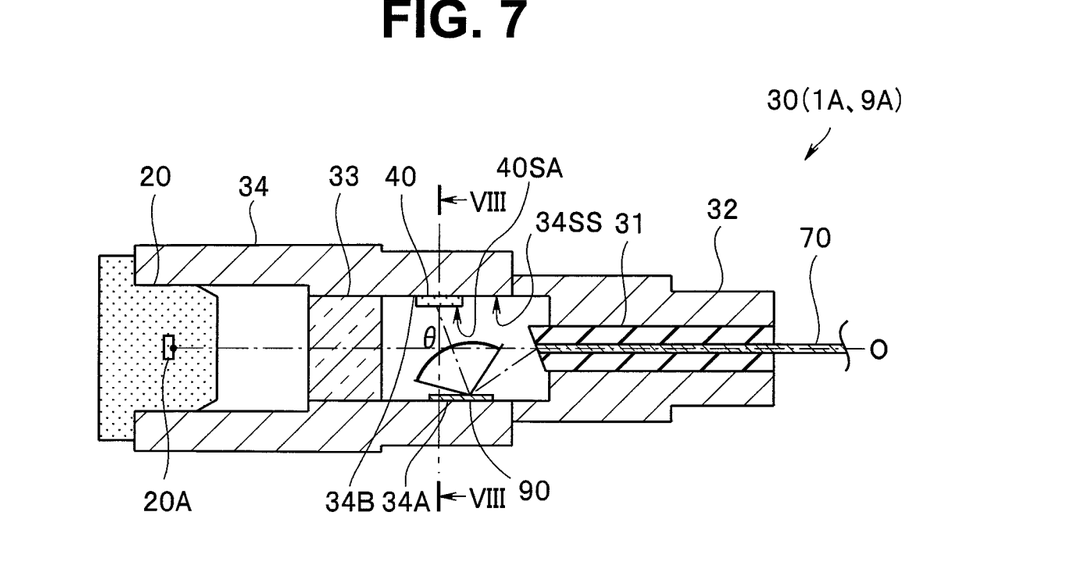
FIG. 7 is a cross-sectional view of a light source apparatus for an endoscope according to Modification 1 of the embodiment.
Figure 8:
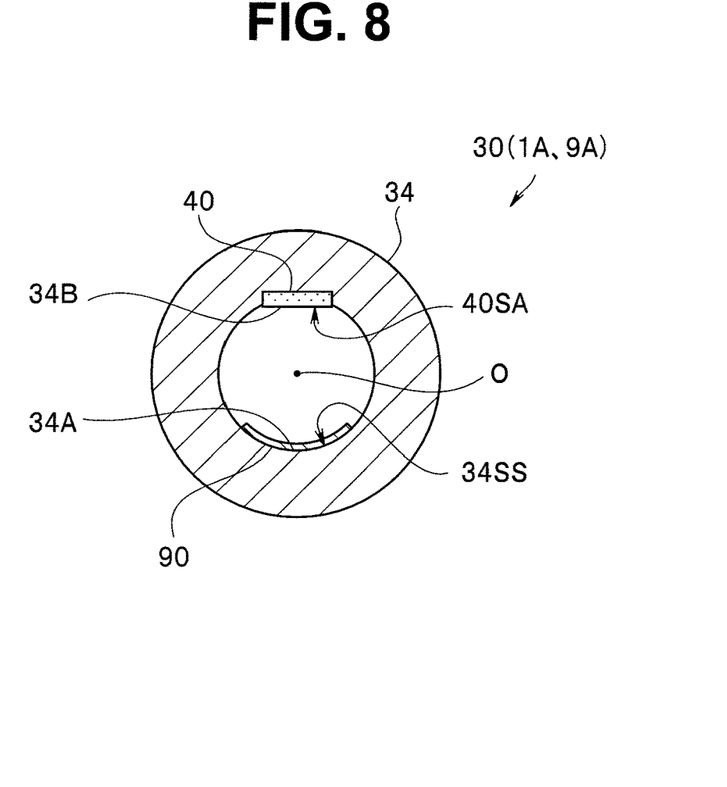
FIG. 8 is a cross-sectional view of the light source apparatus for the endoscope according to Modification 1 of the embodiment taken along line VIII-VIII of FIG. 7.

As illustrated in FIGS. 7 and 8, in the light source apparatus 1A according to the present modification, the reflecting surface is a scattering surface 90 that scatters and reflects the first reflected light, and the second reflected light is the scattered reflected light.

The scattering surface 90 is a first region 34A of the inner surface 34SS on which the first reflected light is directly incident. On the other hand, the optical sensor 40 is disposed in a second region 34B. The second region 34B is located outside the optical path of the emission light collected by the lens 33, that is, on the inner surface 34SS where the emission light collected by the lens 33 is not directly incident, and faces the first region 34A through the optical axis O.

Figure 9:
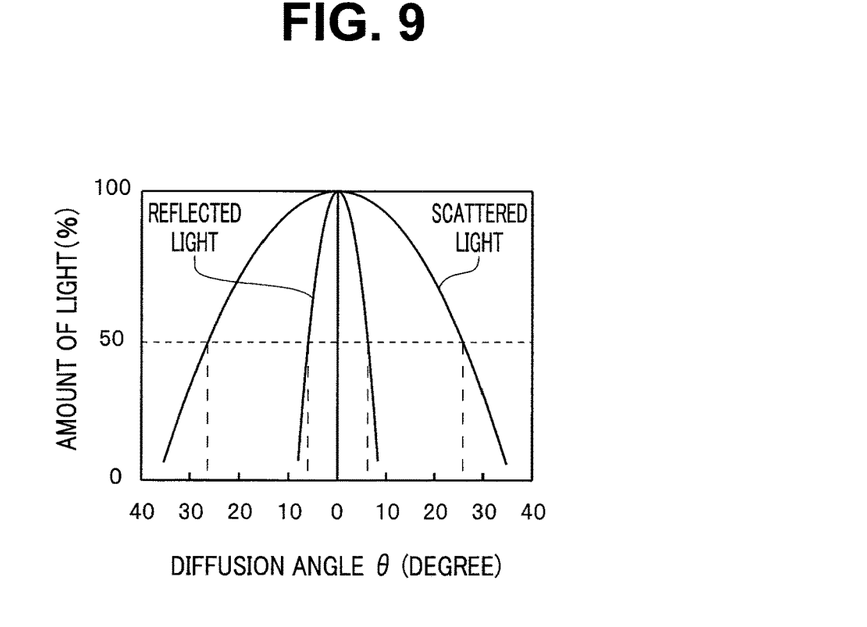
FIG. 9 is a diagram for explaining a scattering angle.

Note that, even when the reflecting surface is a mirror surface, some of the light incident on the reflecting surface is emitted as the scattered light. That is, strictly speaking, all reflected light is scattered reflected light including scattered light. However, in the present specification, the scattered reflected light having a scattering angle θ of less than 10 degrees may be referred to as "reflected light", and the scattered reflected light having a scattering angle θ of 10 degrees or more may be referred to as "scattered light". As shown in FIG. 9, the scattering angle θ is an angle at which the amount of light is 50% or less when the amount of light on the optical axis (central axis) of the emission light is assumed to be 100%.

The scattering angle θ of the scattering surface 90 is preferably 20 degrees or more, and particularly preferably 30 degrees or more. When the scattering angle θ of the scattering surface 90 is as described above, the amount of the second reflected light which is scattered reflected light is easily optimized. Note that the upper limit of the scattering angle θ of the scattering surface 90 is, for example, 60 degrees from a technical point of view.

The scattering surface 90 may be a coated film having uneven surface due to the dispersion of particles, or may be a region where the inner surface 34SS is roughened.

Compared to the first reflected light, the scattered second reflected light (scattered reflected light) not only reduces the amount of light on the optical axis (maximum amount of light), but also greatly widen the optical path (optical path cross-sectional area). Therefore, the amount of light incident on the optical sensor 40 having a predetermined area is also greatly reduced, and the second reflected light has an appropriate amount of light for the optical sensor 40. Accordingly, the light source apparatus 1A can accurately detect the amount of light.

<Modifications 2 and 3 of Embodiment>

Figure 10:
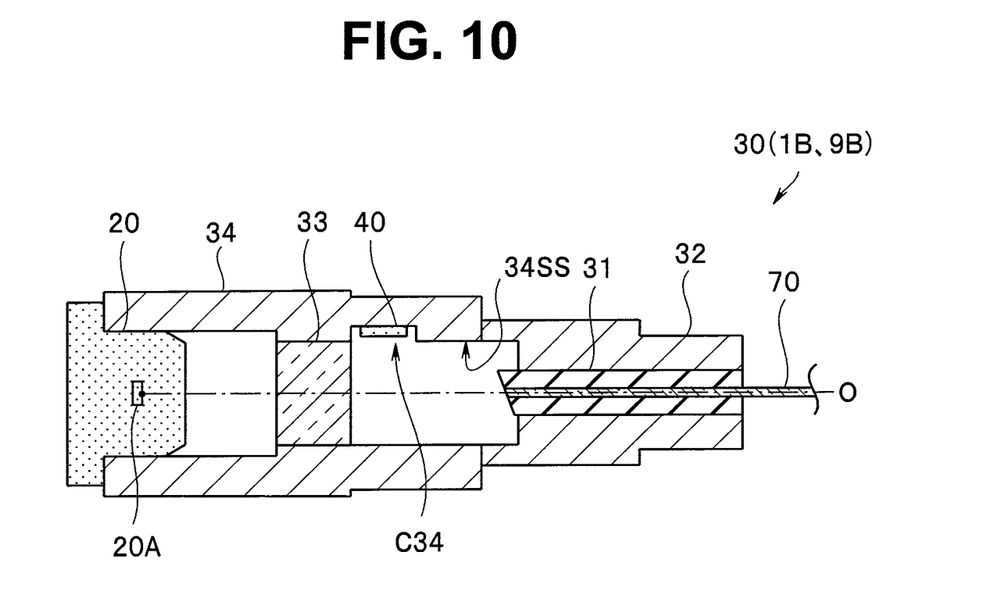
FIG. 10 is a cross-sectional view of a light source apparatus for an endoscope according to Modification 2 of the embodiment.
Figure 11:
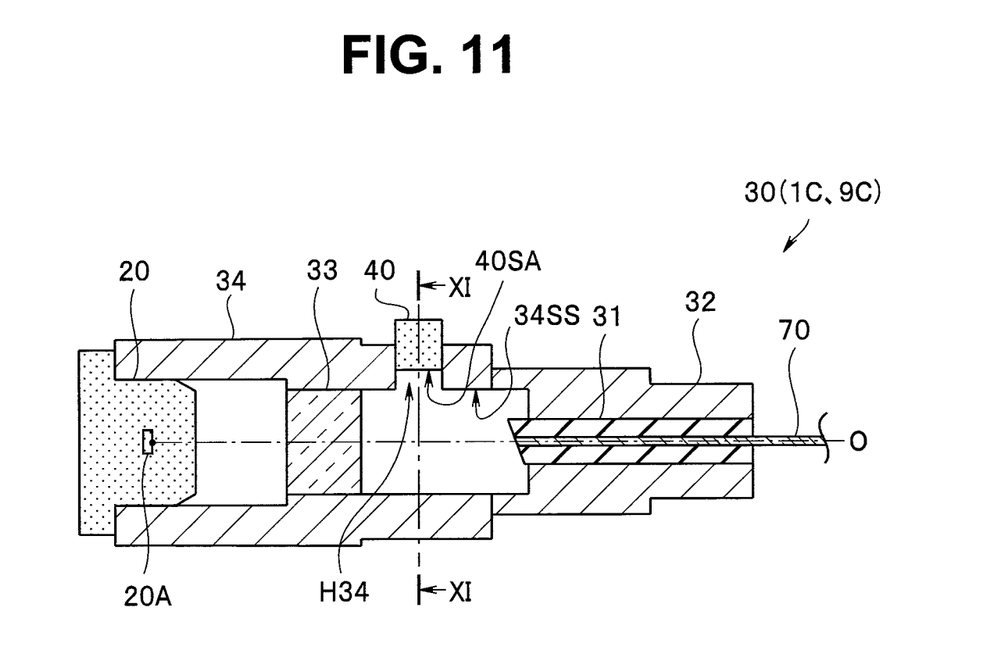
FIG. 11 is a cross-sectional view of a light source apparatus for an endoscope according to Modification 3 of the embodiment.
Figure 12:
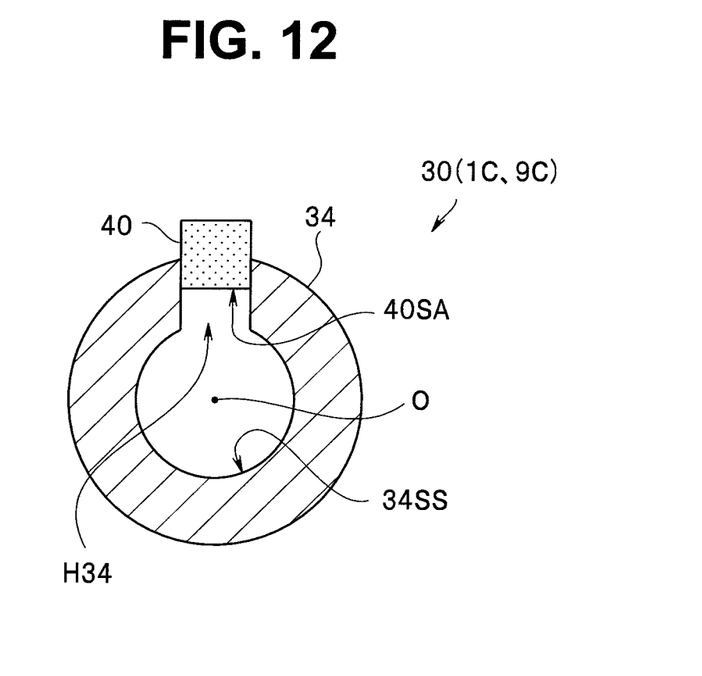
FIG. 12 is a cross-sectional view of the light source apparatus for the endoscope according to Modification 3 of the embodiment taken along line XII-XII of FIG. 11.

As illustrated in FIG. 10, in a light source apparatus 1B according to Modification 2, the optical sensor 40 is disposed in a bottomed recess C34 of the inner surface 34SS of the holder 34. On the other hand, as illustrated in FIGS. 11 and 12, in the light source apparatus 1C according to Modification 3, the optical sensor 40 is disposed in a through-hole H34 which is a recess of the holder 34.

The optical sensor 40 disposed in the recess does not detect light around the optical sensor 40, which may be incident from the side surface.

Note that it is more preferable that the light receiving surface 40SA of the optical sensor 40 be disposed deeper than the opening surface on the inner surface 34SS, of the recess C34 or the through-hole H34.

The optical sensor 40 disposed deeper than the opening surface of the recess C34 also reduces the amount of light that may be incident on the light receiving surface 40SA from an oblique direction.

Since the amount of light incident on the optical sensor 40 is reduced and becomes appropriate for the optical sensor 40, the light source apparatuses 1B and 1C can accurately detect the amount of light.

Note that, in the light source apparatus 1C in which the optical sensor 40 is disposed in the through-hole, it is possible to finely adjust the arrangement position of the optical sensor 40. For example, a drive signal is supplied to the light source 20 to generate emission light for testing. Then, the intensity of the detection signal (photocurrent) outputted by the optical sensor 40 is monitored. While moving the position of the optical sensor 40 in the through-hole H34 orthogonally to the optical axis, the position of the optical sensor 40 is determined so that the detection signal outputted by the optical sensor 40 is optimal. Then, the optical sensor 40 is fixed to the through-hole H34 by, for example, an adhesive (not illustrated).

Since the position of the optical sensor 40 can be finely adjusted, the light source apparatus 1C can detect the amount of light with particularly high accuracy.

<Modification 4 of Embodiment>

Figure 13:
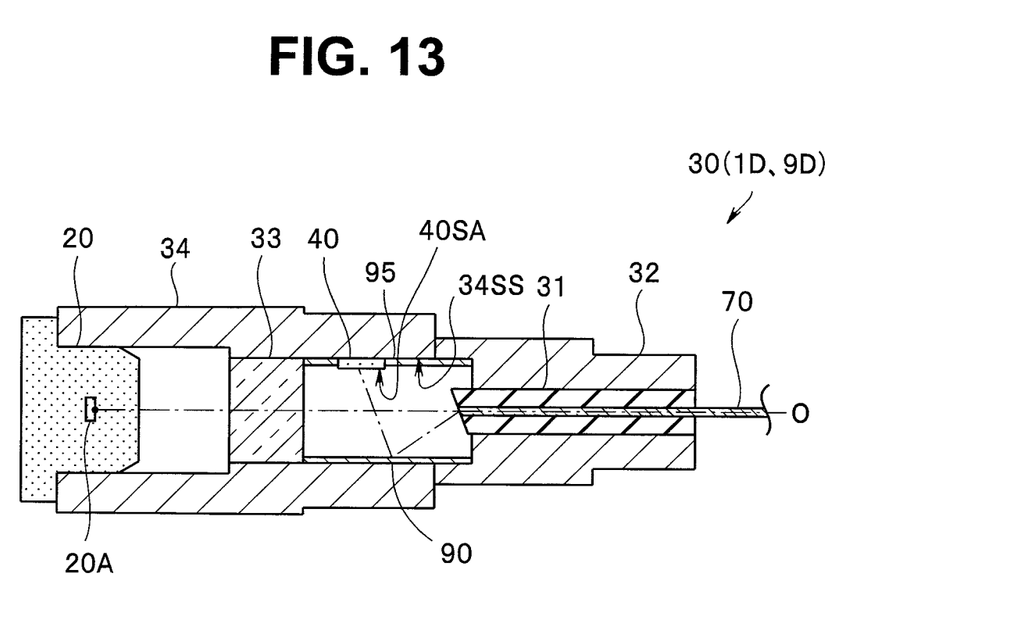
FIG. 13 is a cross-sectional view of a light source apparatus for an endoscope according to Modification 4 of the embodiment.

As illustrated in FIG. 13, in the light source apparatus 1D according to the present modification, a light absorbing member 95 that does not reflect light is disposed around the optical sensor 40. The light absorbing member 95 is a black chrome plating film, a carbon particle-containing resin film, or the like. In the light absorbing member 95, the reflectance of light having a wavelength of emission light is preferably 10% or less, and particularly preferably 5% or less. The reflectance is a ratio of the light, which is not absorbed nor transmitted by the inner surface 34SS and is reflected, to the emission light vertically incident on the machined surface.

When the light absorbing member 95 is disposed around the optical sensor 40, the optical sensor 40 does not detect ambient light incident from the side surface. Since the amount of incident light is reduced and becomes appropriate for the optical sensor 40, the light source apparatus 1D can accurately detect the amount of light.

<Modification 5 of Embodiment>

Figure 14:
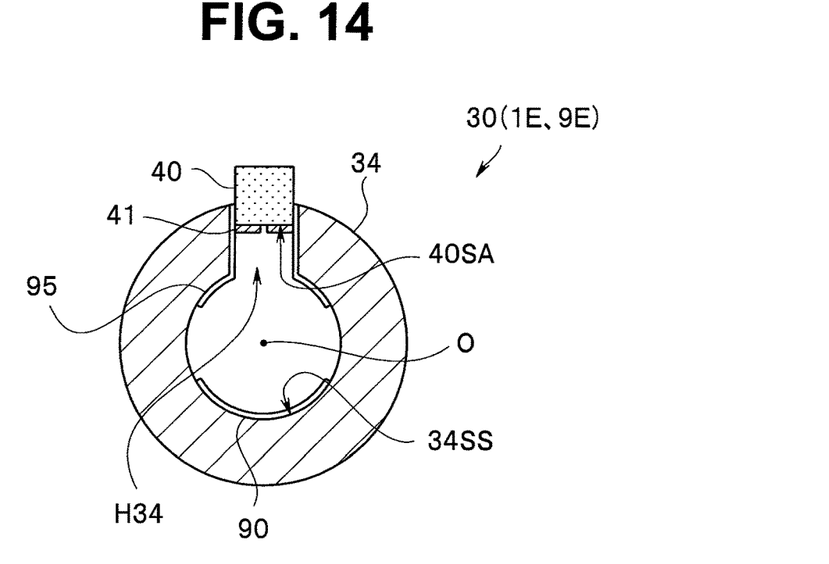
FIG. 14 is a cross-sectional view of a light source apparatus for an endoscope according to Modification 5 of the embodiment.

As illustrated in FIG. 14, in the light source apparatus 1E according to the present modification, the optical sensor 40 includes a light amount reducing member 41 that reduces the amount of incident light.

The light amount reducing member 41 is a metal plate having holes or the like. For example, the amount of light incident on the optical sensor 40 can be made appropriate by selecting the size of the holes or the number of holes formed in the metal plate. Accordingly, the light source apparatus 1E can detect the amount of light with particularly high accuracy.

Figure 15:
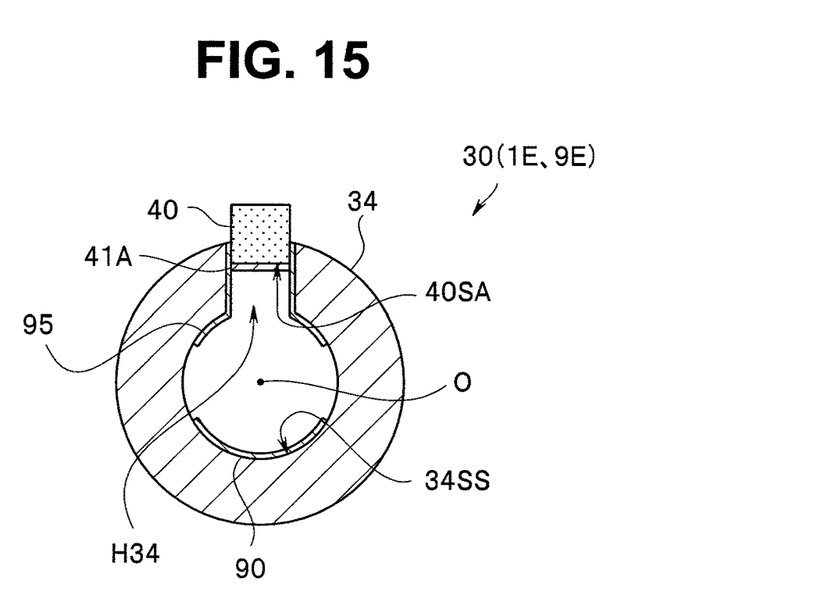
FIG. 15 is a cross-sectional view of another light source apparatus for the endoscope according to Modification 5 of the embodiment.

As illustrated in FIG. 15, the light source apparatus 1E may include a semi-transmissive film that transmits only some of the light, as a light amount reducing member 41A.

<Modification 6 of Embodiment>

Figure 16:
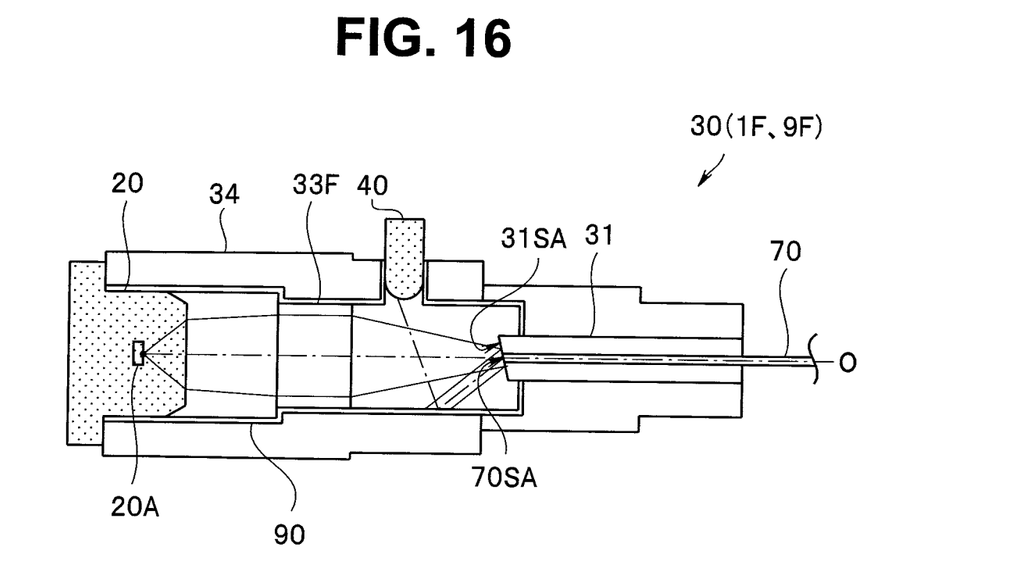
FIG. 16 is a diagram for explaining an optical path of a light source apparatus for an endoscope according to Modification 6 of the embodiment.

As illustrated in FIG. 16, in the light source apparatus 1F according to the present modification, the numerical aperture (NA) of a lens 33F exceeds the numerical aperture (NA) of the optical fiber 70. That is, some of the emission light collected by the lens 33F is incident on and reflected by the ferrule end face 31SA.

Note that, in an optical sensor 40A, the PD is housed in a hemispherical transparent cover member. The optical sensor may be a PD in which a hemispherical condenser lens is disposed.

Although not illustrated, in the light source apparatus 1F in which the emission light is also incident on the ferrule end face 31SA, a reflective film or a light absorbing film for adjusting the amount of light of the first reflected light may be disposed on the ferrule end face 31SA around the fiber end face 70SA in order to adjust the amount of light to be received by the optical sensor 40A.

Further, in the light source apparatus 1F, the entire surface of the inner surface 34SS is the scattering surface 90. Even when the light multiply reflected on the inner surface 34SS is incident on the optical sensor 40A, the amount of light incident on the optical sensor 40A is small and averaged because the multiple reflected light is the scattered reflected light. The light source apparatus 1F can accurately detect the amount of light.

Note that, also in the light source apparatuses 1 and 1A to 1E, the numerical aperture (NA) of the lens 33 may exceed the numerical aperture (NA) of the optical fiber 70. However, in order to ensure the amount of illumination light, it is preferable that the numerical aperture (NA) of the lens 33 be equal to or less than the numerical aperture (NA) of the optical fiber 70.

In a light source apparatus that generally transmits an optical signal, in order to suppress deterioration of the optical signal due to multiple reflections between the lens and the end face of the optical fiber, the fiber end face needs to be inclined with respect to a plane perpendicular to the optical axis of the optical fiber. However, in the light source apparatus for transmitting the illumination light, the fiber end face 70SA may be polished perpendicular to the optical axis O of the optical fiber 70. In the light source apparatus in which the fiber end face 70SA is perpendicular to the optical axis O of the optical fiber 70, most of the emission light is incident on the optical fiber 70, so that the transmission efficiency is high. Even when the emission light is vertically incident on the fiber end face 70SA, some of the emission light is reflected by the fiber end face 70SA and becomes the first reflected light.

Needless to say, when one light source apparatus has the respective configurations of the light source apparatuses 1A to 1F together, the one light source apparatus also has the respective effects of the light source apparatuses 1A to 1F. Needless to say, the endoscopes 9A to 9F having the light source apparatuses 1A to 1F have the effects of the endoscope 9 and further have the effects of the light source apparatuses 1A to 1F.

The above description has described the light source apparatuses and the like that emit a large amount of illumination light, in which the effects of the present invention are particularly remarkable. However, a light source apparatus and the like that output an optical signal having a relatively small amount of light can also yield the same effects as those of the light source apparatuses 1 and 1A to 1F and the endoscopes 9 and 9A to 9F according to the embodiment and modifications.

The present invention is not limited to the embodiment, the modifications, and the like described above, and various modifications, combinations, and applications can be made without departing from the spirit and scope of the present invention.

What is claimed is:

1. A light source apparatus for an endoscope, comprising:
    an optical fiber having a fiber end face, the optical fiber being configured to guide emission light emitted from a light source and incident on the fiber end face;
    a ferrule having a ferrule end face, the ferrule having an opening of a through-hole on the ferrule end face, the optical fiber being inserted into the through-hole;
    a holder to which the ferrule is fixed, the holder having a reflecting surface configured to reflect first reflected light to thereby emit second reflected light, the first reflected light being the emission light reflected on the fiber end face; and
    an optical sensor having a light receiving surface configured to receive the second reflected light, the optical sensor being disposed between the light source and the fiber end face and in a region facing the reflecting surface through an optical axis.

2. The light source apparatus for the endoscope according to claim 1, further comprising a lens fixed to the holder, the lens being configured to collect the emission light on the fiber end face, wherein
    the holder has an inner surface surrounding a space including an optical path of the emission light to be collected by the lens, and
    the optical sensor is disposed between the lens and the fiber end face.

3. The light source apparatus for the endoscope according to claim 2, wherein the reflecting surface is a scattering surface configured to scatter and reflect the first reflected light, and the second reflected light is scattered reflected light.

4. The light source apparatus for the endoscope according to claim 3, wherein
    the scattering surface is a first region on the inner surface on which the first reflected light is directly incident, and
    the optical sensor is disposed in a second region on the inner surface, the second region being located outside the optical path and facing the first region through the optical axis.

5. The light source apparatus for the endoscope according to claim 2, wherein the optical sensor is disposed in a recess on the inner surface.

6. The light source apparatus for the endoscope according to claim 5, wherein, in the optical sensor, the light receiving surface is disposed deeper in the recess than an opening surface of the recess.

7. The light source apparatus for the endoscope according to claim 2, further comprising a light absorbing member disposed around the optical sensor, the light absorbing member having a reflectance of 10% or less.

8. The light source apparatus for the endoscope according to claim 2, wherein the optical sensor includes a light amount reducing member configured to reduce an amount of the second reflected light incident on the optical sensor.

9. The light source apparatus for the endoscope according to claim 2, wherein
    the fiber end face is inclined with respect to a plane perpendicular to the optical axis, and
    the first reflected light is emitted in a direction of a position facing an arrangement position of the optical sensor through the optical axis.

10. The light source apparatus for the endoscope according to claim 2, wherein a numerical aperture of the lens is equal to or less than a numerical aperture of the optical fiber.

11. The light source apparatus for the endoscope according to claim 2, wherein
a numerical aperture of the lens exceeds a numerical aperture of the optical fiber, and
the first reflected light includes the emission light reflected by the ferrule end face.

12. The light source apparatus for the endoscope according to claim 1, further comprising a controller configured to adjust an amount of the emission light by controlling the light source according to an output of the optical sensor.

13. The light source apparatus for the endoscope according to claim 1, wherein the emission light is illumination light.

14. An endoscope comprising a light source apparatus for the endoscope, wherein the light source apparatus for the endoscope comprises:
an optical fiber having a fiber end face, the optical fiber being configured to guide emission light emitted from a light source and incident on the fiber end face;
a ferrule having a ferrule end face, the ferrule having an opening of a through-hole on the ferrule end face, the optical fiber being inserted into the through-hole;
a holder to which the ferrule is fixed, the holder having a reflecting surface configured to reflect first reflected light to thereby emit second reflected light, the first reflected light being the emission light reflected on the fiber end face; and
an optical sensor having a light receiving surface configured to receive the second reflected light, the optical sensor being disposed between the light source and the fiber end face and in a region facing the reflecting surface through an optical axis.

15. An endoscope system comprising an endoscope and a light source apparatus for the endoscope, wherein the light source apparatus for the endoscope comprises:
an optical fiber having a fiber end face, the optical fiber being configured to guide emission light emitted from a light source and incident on the fiber end face;
a ferrule having a ferrule end face, the ferrule having an opening of a through-hole on the ferrule end face, the optical fiber being inserted into the through-hole;
a holder to which the ferrule is fixed, the holder having a reflecting surface configured to reflect first reflected light to thereby emit second reflected light, the first reflected light being the emission light reflected on the fiber end face; and
an optical sensor having a light receiving surface configured to receive the second reflected light, the optical sensor being disposed between the light source and the fiber end face and in a region facing the reflecting surface through an optical axis.

* * * * *